United States Patent [19]
Ritter

[11] Patent Number: 5,372,787
[45] Date of Patent: Dec. 13, 1994

[54] STERILIZING CONTAINER FOR MEDICAL AND SURGICAL INSTRUMENTS AND APPARATUS

[76] Inventor: Ralf Ritter, Schwibbogenmauer 18, 86150 Augsburg, Germany

[21] Appl. No.: 120,000

[22] Filed: Sep. 13, 1993

[30] Foreign Application Priority Data

Sep. 12, 1992 [DE] Germany .................. 9212315[U]
Jun. 15, 1993 [DE] Germany .................. 9308769[U]

[51] Int. Cl.⁵ .................. A61L 2/06; B65D 51/16
[52] U.S. Cl. .................. 422/119; 422/297; 422/300; 220/87.1; 220/324; 206/363; 206/439; 206/507; 206/508
[58] Field of Search .............. 422/294, 297, 300, 310, 422/119; 436/1; 292/247; 220/324, 87.1; 206/363, 439, 507, 508; 435/313

[56] References Cited

U.S. PATENT DOCUMENTS

4,915,913  4/1990  Williams et al. .................. 422/119
5,080,874  1/1992  Nichols .................. 422/300

*Primary Examiner*—David A. Redding
*Attorney, Agent, or Firm*—Klaus J. Bach

[57] ABSTRACT

In a sterilizing container for medical and surgical instruments comprising a box with a bottom part and a cover for sealing the bottom part in a germ-tight manner, the side walls of the bottom part of the box have openings covered on the outside with germ-tight but sterilization gas permeable filter layers which are held in position by retaining plates mounted on the side walls, the cover of the box being locked to the bottom part by a locking structure formed at one end of the box at which the cover and bottom part includes retaining structures receiving a safety tag which covers the locking structure when the cover is closed in such a way that the safety tag is firmly positioned in front of the locking structure and the locking structure is only accessible by destroying the safety tag.

17 Claims, 8 Drawing Sheets

STERILIZING CONTAINER FOR MEDICAL AND SURGICAL INSTRUMENTS AND APPARATUS

BACKGROUND OF THE INVENTION

German Utility Model 91 05 867 is directed to a sterilizing container for particular medical and surgical instruments and apparatus, which consists of a rigid box of sterilizing temperature-resistant plastic material which can be subjected to multiple sterilizing processes, and which includes a bottom part with a cover which cooperates with the bottom so as to close the box in a germ-tight manner but which has wall passages with filter layers making it permeable for sterilizing vapors or sterilizing gas.

The wall passages are formed in the side walls of the bottom part and the filter layers are embedded in between the side walls and an insert disposed in the bottom part and having passages corresponding to the corresponding passages formed in the bottom part side walls. The cover is mounted on the bottom part by means of hinges and can be sealed, when closed, by an adhesive label.

It is the object of the present invention to provide such a sterilizing container which however is improved with regard to its handling, to the safety of the sterilizing state, up to the use of the instruments and apparatus contained therein, and to the capability of easily verifying the sterility condition of its contents.

SUMMARY OF THE INVENTION

In a sterilizing container for medical and surgical instruments comprising a box with a bottom part and a cover for sealing the bottom part in a germ-tight manner, the side walls of the bottom part of the box have openings covered on the outside with germ-tight but sterilization gas permeable filter layers which are held in position by retaining plates mounted on the side walls, the cover of the box being locked to the bottom part by a locking structure formed at one end of the box at which the cover and bottom part include retaining structures receiving a safety tag which covers the locking structure when the cover is closed in such a way that the safety tag is firmly positioned in front of the locking structure and the locking structure is only accessible by destroying the safety tag.

The advantages achieved by the arrangement according to the invention are described in detail in the following description of a preferred embodiment on the basis of the attached drawings.

DESCRIPTION OF THE PREFERRED EMBODIMENTS

Figure 1:
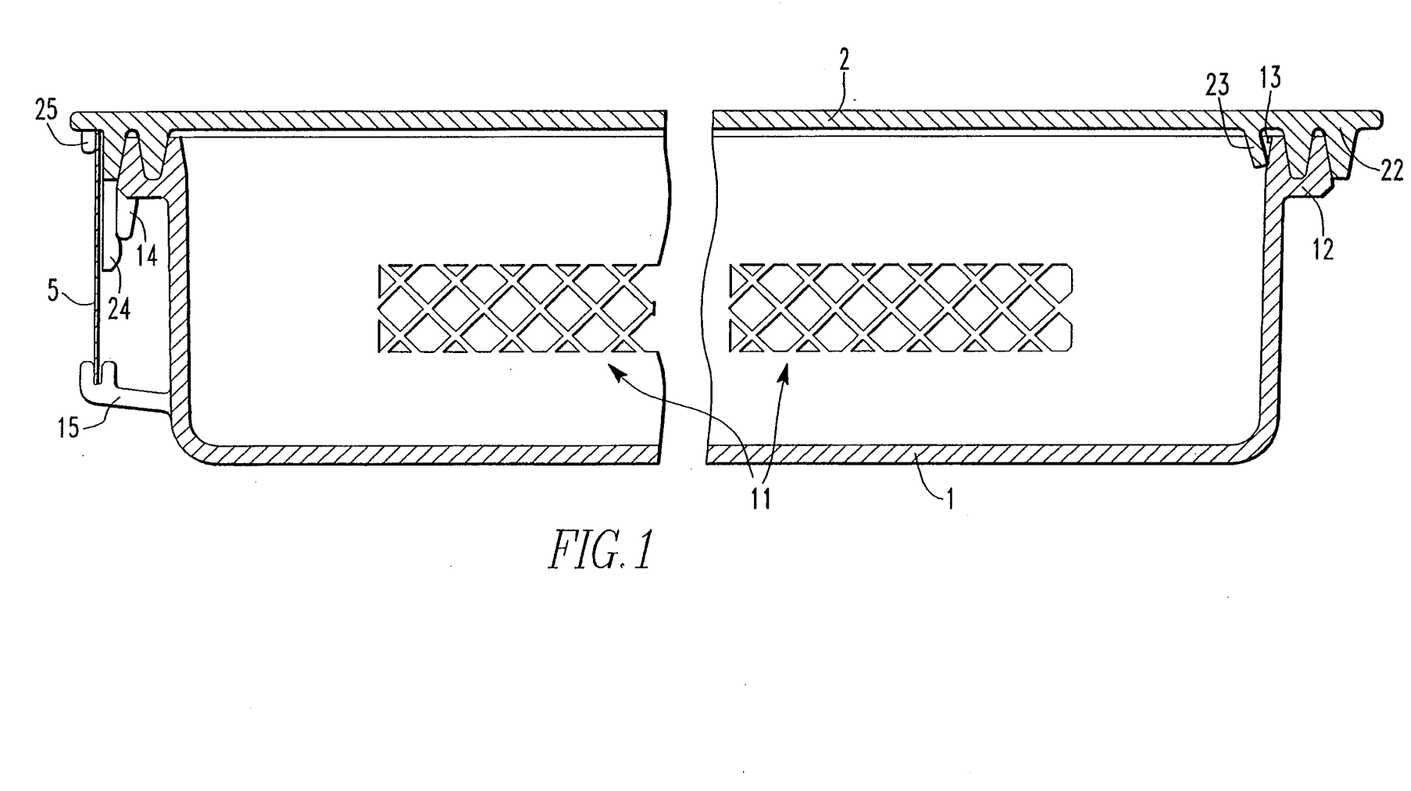
FIG. 1 is a longitudinal cross-sectional view of the container according to the invention with the cover closed.
Figure 2:
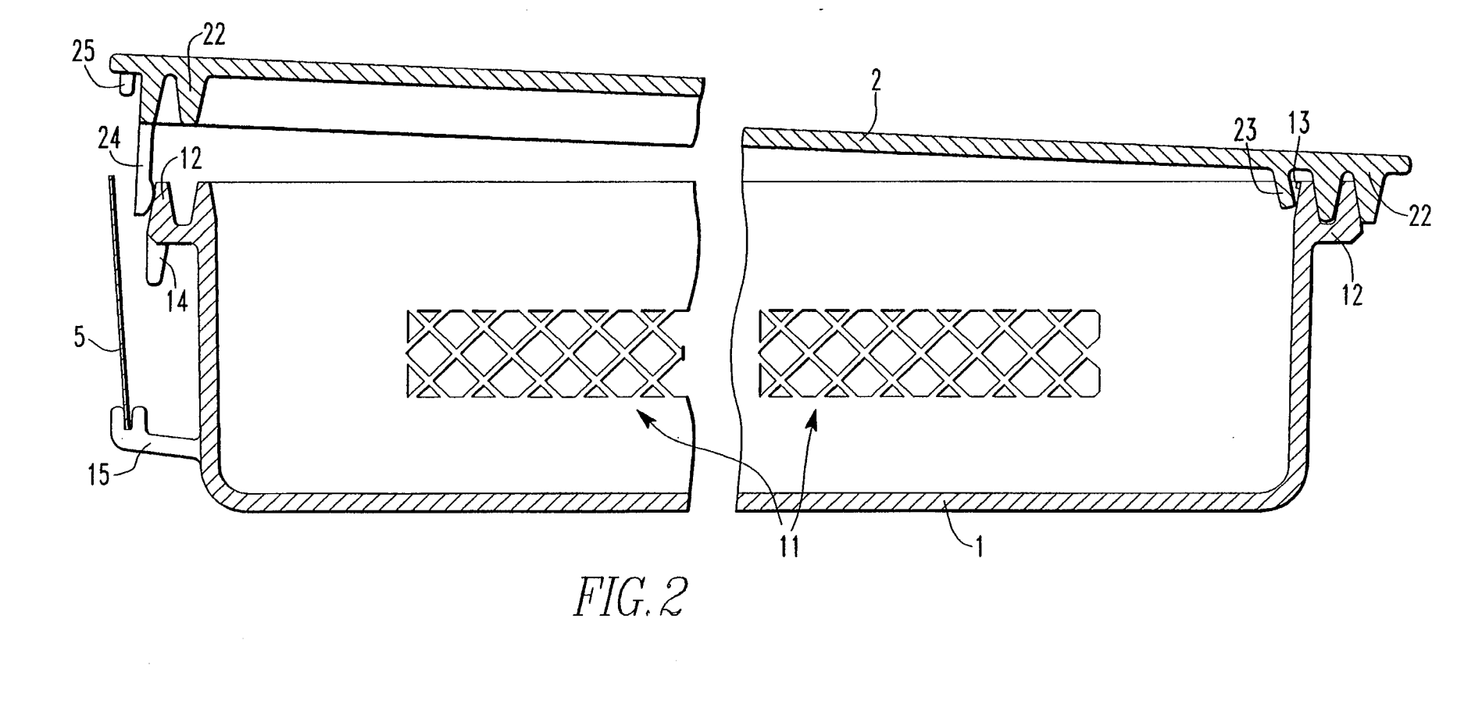
FIG. 2 is a longitudinal cross-sectional view similar to that of FIG. 1 with the cover being almost closed.

In order to make the details of interest clearly recognizable, the representations of FIGS. 1 to 5 are given at a size ratio of about 2:1, that is, four times the actual size, wherein however the representations of FIGS. 1 and 2 are shortened by elimination of the center section.

Figure 3:
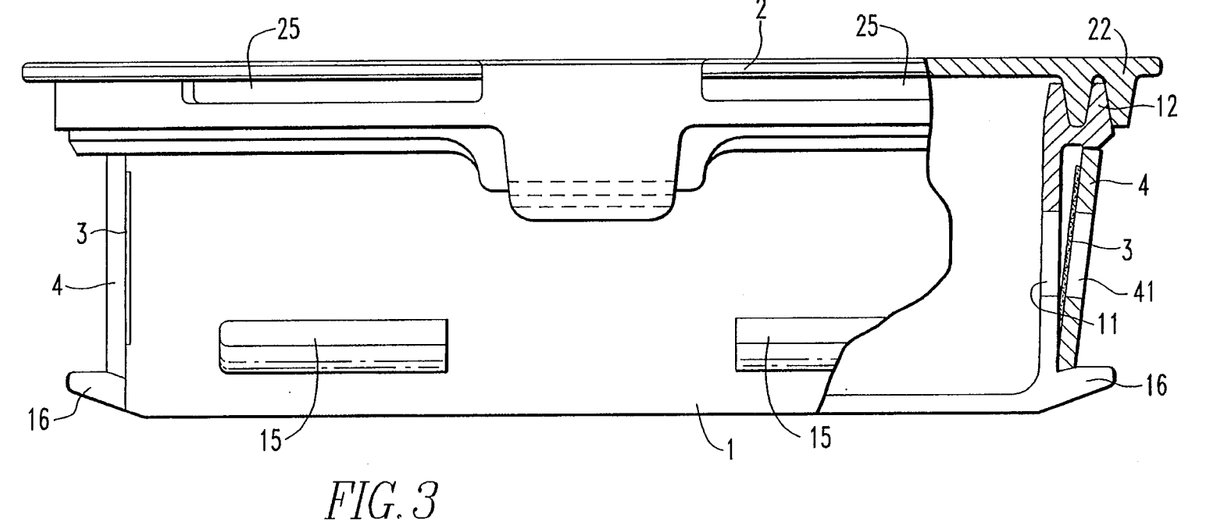
FIG. 3 is a front view of the closed container without labels and with a side wall portion shown in cross-section.

FIG. 1 shows, in longitudinal cross-section, a container according to the invention, that is, a sterilization box which consists of a bottom part 1 and a cover 2 disposed thereon. The longitudinal side walls have a number of lattice-like openings 11 which, as it may be seen from FIG. 3, are covered on the outside by a germ-tight but sterilization gas permeable filter layer 3 retained by a retaining plate 4 which is mounted on the respective longitudinal side wall and includes openings 41 corresponding to the openings 11 in the side wall.

The lower part is provided at its upper edge with a double-web profile structure 12 extending therearound which is in engagement with a corresponding profile structure 22 extending around the cover 2, the two profile structures together forming a germ-tight closure.

As can be seen in the cross-sectional representations of FIGS. 1 and 2 the cover 2 has, at its rear narrow side, in addition to the double web profile structure 22 a backwardly inclined rib 23 which engages a knub-like projection 13 formed on the inner side of the double web profile structure 12 of the narrow back end of the bottom part 1, when the cover 2 is closed as shown in FIG. 1 so that lifting of the cover 2 from the bottom part 1 is not possible at the back end of the box. When placing the cover 2 onto the bottom part 1 the cover is therefore first placed onto the bottom part in an inclined position as shown in FIG. 2, in which the back end is engaged with the respective top edge of the bottom part and the cover is then tilted downwardly at the narrow front end whereby the inclined rib 23 comes to rest under the projection 13.

At its narrow front end the cover 2 is provided with a locking strap 24 which is formed integrally with, and in the center of, the cover 2 so as to extend from the double web profile structure 22 and which, because of its length and the properties of plastic material, is elastic and adapted to engage a projection 14 formed on the underside of the adjacent portion of the double web profile structure of the bottom part when the cover is fully closed and firmly disposed on the bottom part (see FIG. 1). During closing of the cover (see FIG. 2) the locking strap 24 slides down along the outside of the double web profile structure 12 and the projection 14 extending therefrom.

At the front end of the box, that is, at the front narrow ends of the lower portion 1 and the cover 2, there are provided strip-like support profile structures 15 and 25 which include mounting grooves for the reception of a safety tag 5. The safety tag 5 may consist, for example, of rigid cardboard and is shown in FIGS. 1 and 2 in a side view and in FIGS. 4 and 5 in a frontal view. During closing of the cover 2 the safety tag 5 is first inserted with its lower edge into the support profile 15 of the bottom part 1 and, during closure of the front end of the cover 2 (see FIG. 2) is held against the strap 24 so that the upper edge of the safety tag 5 enters the groove in the upper support profile structure 25 of the cover 2 when the cover is pushed down into closing position.

Figure 4:
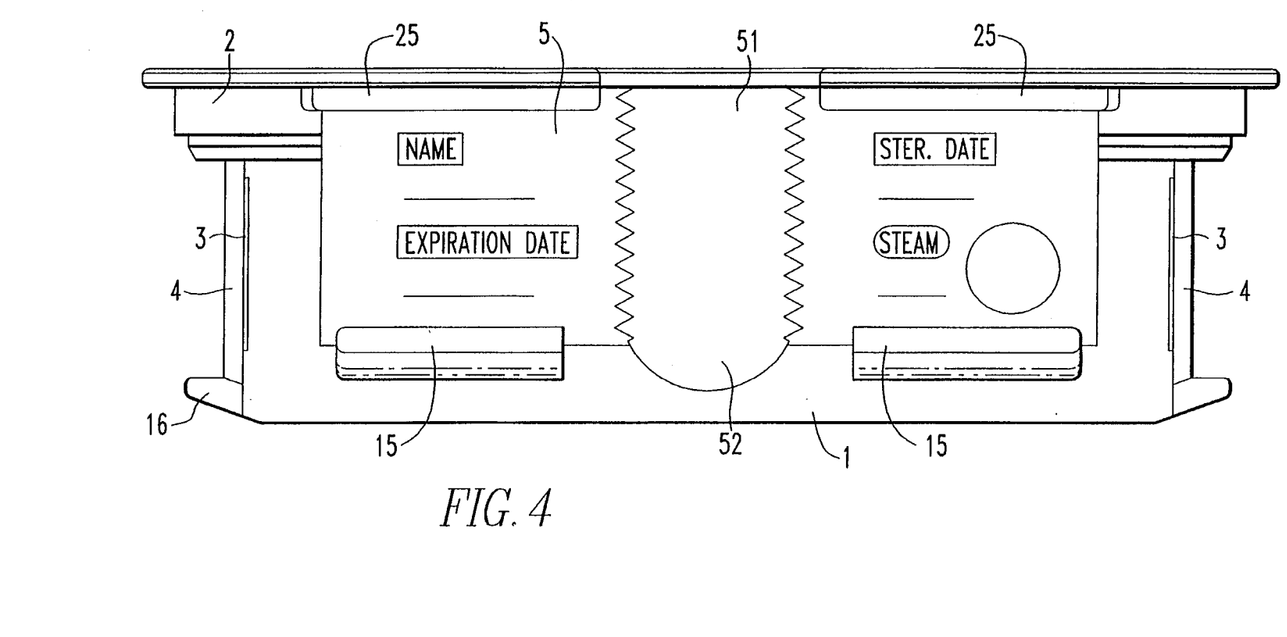
FIG. 4 is a front view of the closed container with the labels applied.

As shown on the left side of FIG. 3 by a dashed line, the groove receiving the safety tag 5 is closed at the outer ends of the upper support profile structure 25 so as to form slide locking members such that the safety tag 5 is retained and cannot slide sidewardly out of the retaining grooves when the cover is closed. The safety tag 5 covers the locking strap 24 of the cover so that the locking strap is not accessible after the box is closed and the box cannot be opened without destroying the safety tag. This is clearly apparent from FIGS. 3 and 4 wherein FIG. 3 is a front view of the box with the cover closed and the safety tag removed to show the locking strap 24, whereas FIG. 4 is a similar view with the safety tag 5 in place and covering the locking strap 24.

Figure 5:
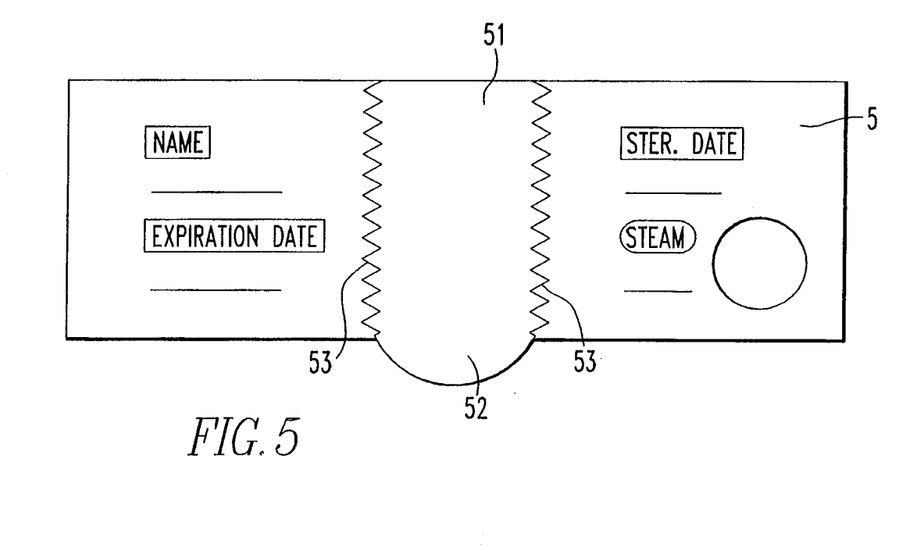
FIG. 5 shows separately the safety label shown in FIG. 4 applied to the container.

FIG. 5 shows the safety tag along for explanation: The safety tag carries various data which, in this connection, are of no particular interest and has in its center a pull-off tongue 51 with a lower semicircular extension 52 facilitating grasping thereof with two fingers. As shown the pull-off tongue 51 is provided at opposite sides with serrated punched impressions 53 which leave it connected to the remainder of the tag 5 but which facilitate tearing off the pull-off tongue 51 by pulling at the extension 52 when the box is to be opened. Then the locking strap 24 becomes accessible and the cover can be opened.

From FIG. 3 it can further be seen how the retaining plates 4 are engageably supported on the two longitudinal side walls of the bottom part 1 for retaining the filter layers 3. Outside, extending along the bottom of each longitudinal side wall, there is a retaining web 16 with an inclined seating surface on which a correspondingly inclined lower edge surface of the retaining plate 4 rests, and on top there is provided on the underside of the web profile structure 12 a slight projection 17 cooperating with the rounded top edge of the retaining plate 4. The retaining plate 4 with the filter layer mounted thereon, for example by cementing, is first placed with its inclined lower edge onto the retaining web 16 as shown in cross-section in the right half of FIG. 3 and is then pressed inwardly at its top so that the top edge is resiliently engaged behind the projection 17.

The box according to the invention provides for two essential operational advantages as is apparent from the above description.

First, it is impossible to open the cover of the box without destroying the safety tag so that possible discontinuation of the sterilized state of the content is noticeable, that is, in other words, an undamaged safety tag on the closed box indicates the presence of the original sterile state.

Second, the filter layers 3 which are supported on the outside by means of engageable support plates 4 provide for smooth inner box surfaces without inserts or other structures which facilitates handling of the medical instruments when placing them into, or removing them from, the box. Still the filter layers are easily replaceable when necessary since they are mounted on the removable support plates 4.

FIGS. 6 to 9 show another embodiment of the container according to the invention which is distinguished from the arrangement according to FIGS. 1 to 5 essentially by a two-part cover design that has additional advantages especially with regard to insuring the sterilized state of the content up to its use.

Figure 6:
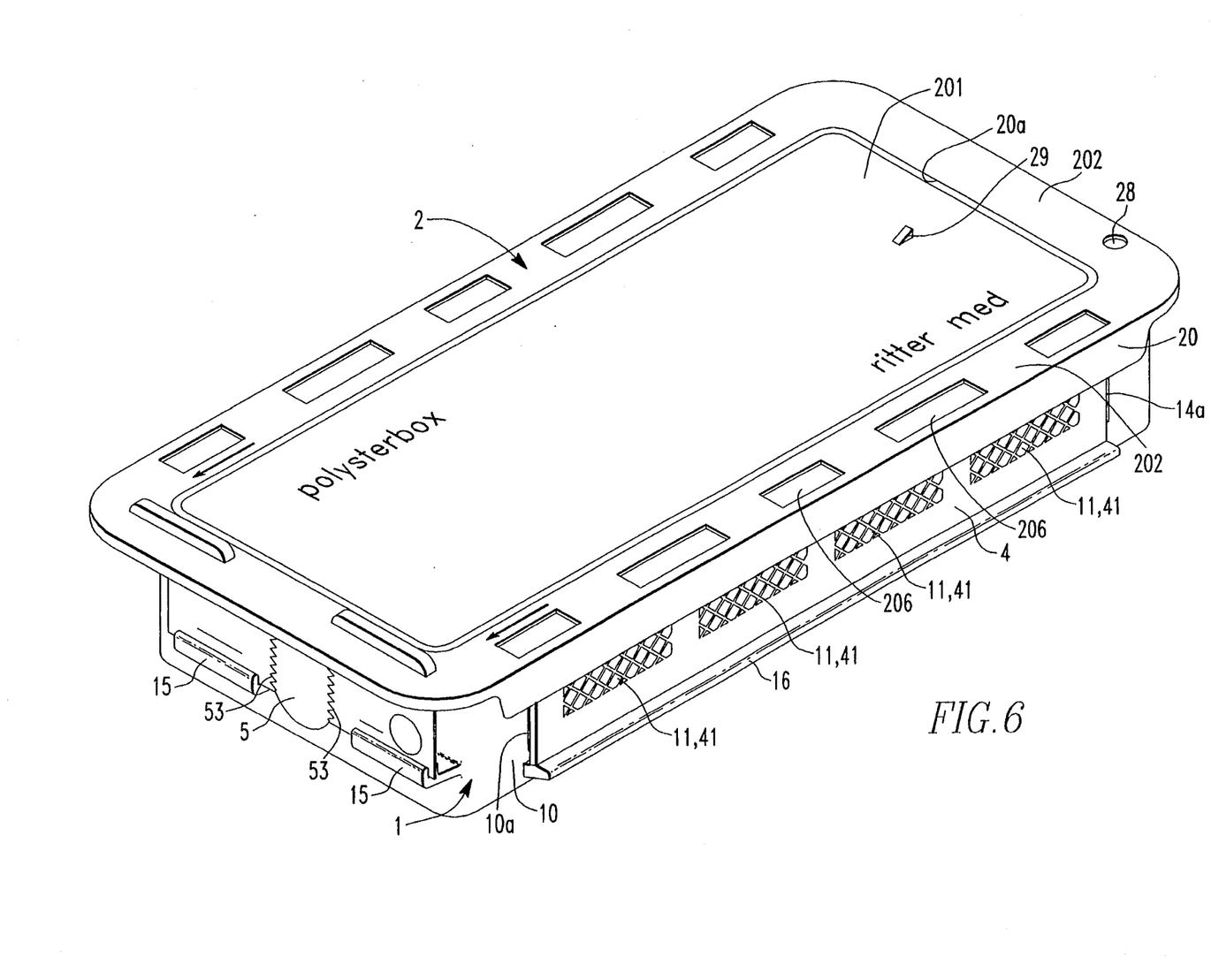
FIG. 6 is a perspective view of another embodiment of a sterilization box according to the invention with closed and locked cover.

FIG. 6 shows a container in accordance with the other embodiment of the invention in fully closed state. Again, both longitudinal sides of the bottom part 1 are provided with a number of lattice-like openings 11 which include a germ-tight but sterilization gas permeable filter layer 3.

Figure 7:
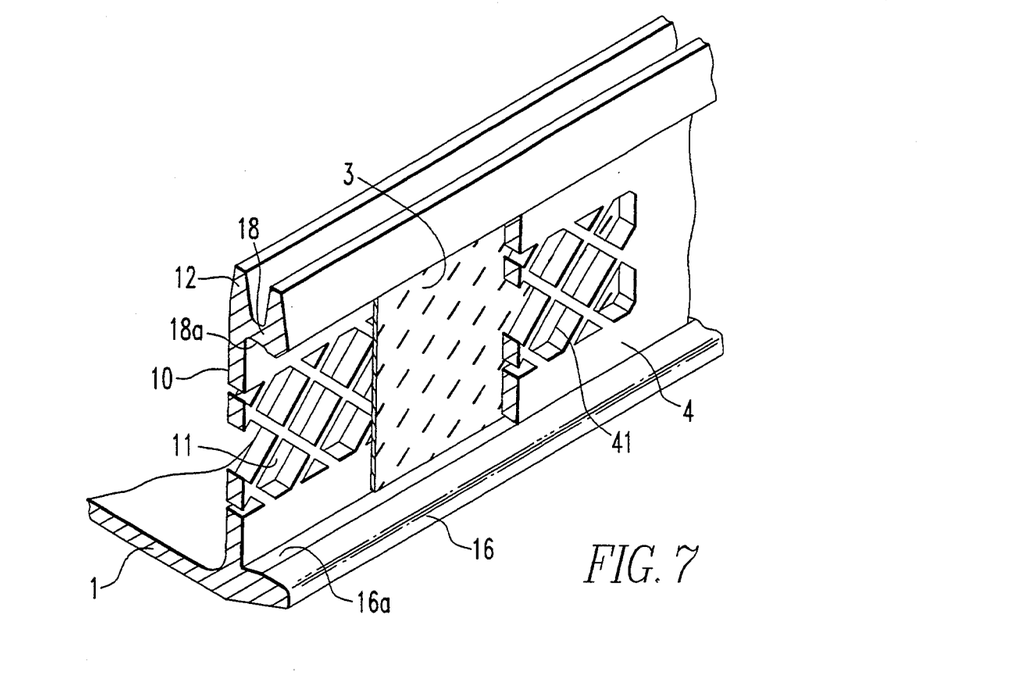
FIG. 7 is a perspective view showing the design of the longitudinal side wall of the bottom part of the sterilization box according to FIG. 6.

The side wall arrangement with the lattice-like openings 11 is shown in detail in FIG. 7. As can be seen the side walls are—like in the first-described embodiment—of sandwich-like design and consist of a wall portion 10 of the bottom part which includes the lattice-like opening 11, a filter mat 3 which is disposed on the outside of the wall portion 10 and which is germ-tight but sterilizing gas permeable and an outer retaining plate 4 which is disposed outside on top of the filter layer and retains the filter layer in contact with the outer surface of the wall portion 10 and which also is provided with lattice-like openings 41 which, in shape and arrangement, correspond to the lattice-like openings 11 of the side wall portion 10 so as to be congruent therewith. The retaining plate 4 again is engageable at its lower and upper edges in corresponding slight recesses 16a and 18a of a lower retaining web 16 and an upper ledge 18, both projecting outwardly at the lower and upper ends of the side wall portion 10. The retaining web 16 has an inclined recess 16a so as to provide an inclined seating surface for the correspondingly inclined lower edge of the retaining plate 4, and the upper ledge 18 has a recess 18a which is an essentially rectangular groove adapted to receive the rounded top edge of the retaining plate 4 for engagement therein. The retaining plate 4 is first placed with its lower edge onto the seating surface of the lower recess 16a and the upper edge is then pressed inwardly onto the wall portion until the upper edge is engaged in the upper recess 18a. The geometrical conditions at the upper and lower edge areas of the retaining plate 4 and the recesses 16a and 18a are simple and easily provided by any person with normal skill in the field in such a manner that the engaged retaining plate 4 compreses the filter mat 3 and presses it against the wall portion 10 with a predetermined force.

It is quite apparent that the engagement recesses 16a and 18a and the corresponding edge areas of the retaining plate 4 may be shaped in any other suitable manner.

By means of the engageable retaining plates 4 the filter mats 3 on both sides of the box can be replaced from time to time, that is, after a predetermined number of sterilizing procedures.

Figure 8:
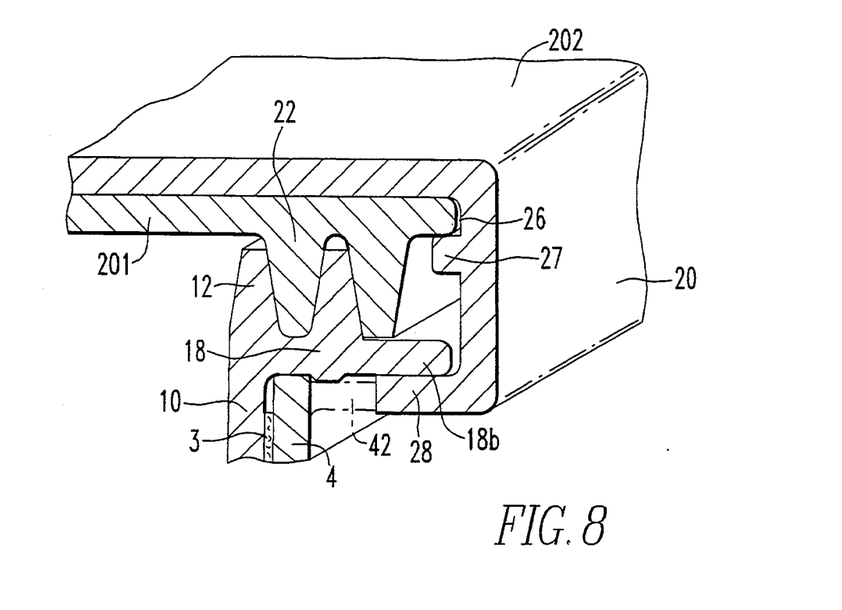
FIG. 8 shows the design of the two-component cover and the cover locking mechanism.

The side walls of the bottom part 1 have, again as shown in FIGS. 7 and 8, at their upper ends, upwardly projecting double profile structures 12 extending around the box and being received in a corresponding downwardly projecting double profile structure 22 formed on the underside of the edge area of a cover member 201 and forming therewith a germ-tight closure.

As already mentioned the cover 2 is a two-part structure and, as can be seen from FIG. 8, consists of the cover member 201 which is provided with the double profile structure 2 and a mounting frame 202. The cover member 201 and the mounting frame 202 are longitudinally movable relative to one another over a predetermined distance. As shown in FIG. 8 the longitudinal edges of the plate-like cover member 201 are guided in a groove 26 formed in the side rim portion 20 of the mounting frame 202 so as to be longitudinally movable therein, the groove 26 consisting of a continuous or interrupted ledge 27, that is, it may consist only of a series of spaced inwardly extending projections. In order to save material and weight, the mounting frame 202 is formed only as a relatively narrow frame structure extending circumferentially around the cover member as shown in FIG. 6, the dimensions of the center cavity within the mounting frame and the shape of the inner edge 20a of the mounting frame 202 corresponding to the outer dimensions of the bottom of the bottom part 1 so that the cavity defined in the mounting frame 202 together with the surface of the cover member 201 form a depression capable of receiving the bottom area of another box which is then firmly retained and prevented from moving horizontally in any direction. In this manner several boxes can be safely disposed on top of one another during the sterilization procedure.

As further shown in FIG. 8 the upper edges of the side walls of the bottom part 1 which carry the double web profile structure 12 have outwardly extending projections 18b of a predetermined limited length. Also, the downwardly extending rim portion 20 of the mounting frame 202 is provided with a corresponding number of inwardly extending projections 28, with about the same longitudinal dimension as the projections 18b, wherein the dimensions, that is, the fit is so selected that the projections 28 of the mounting frame 202 engage the projections 18b of the bottom part 1 with a predetermined elastic tension and deformation so that the double web profile structure 22 of the cover member 201 is forced into tight and well sealing engagement with the double web profile structure 12 of the bottom part. FIG. 6 shows the sterilizing box with both cover parts in such closed position wherein the cover member 201 is locked in closed position onto the bottom part by the mounting frame 202. In this position the cover parts safety lock openings formed in the rear narrow sides of the rim area of the cover member 201 and the mounting frame 202 are in alignment so that, in this locked position, the two parts can be provided with a seal whose presence is a further indication that the sterilized container was not tampered with.

The length of the spaces between the projections 18b of the bottom part 1 is preferably substantially larger than the length of the projections 28 of the mounting frame 202. Distributed over the length of the longer side of the box, three projections 18b and projections 28 with a length of 1.0 to 1.5 cm each are, for example, sufficient. Unlocking of the cover 2 from the bottom part 1 can be accomplished in that the mounting frame 202 is moved longitudinally relative to the cover member 201 by an appropriate distance (see arrows in FIG. 6) whereupon the cover 2, that is, the cover member 201, can be lifted off from the bottom part 1 together with the longitudinally movable mounting frame associated therewith because the projections 28 of the mounting frame 202 can be moved up through the spaces between the projections 18b of the upper ledge 18 of the bottom part 1.

It is noted that stops are provided on the mounting frame 202 and on the cover member 201 so as to cooperate to limit relative longitudinal movement between the two cover parts to the amount required. Nevertheless the two cover parts can easily be assembled and also disassembled by pulling them apart slightly resiliently at a narrow end to permit the cooperating stops, which limit relative movement, to pass by one another whereupon the cover member 201 is simply slidable out of the mounting frame 202 in longitudinal direction.

As can be seen from FIG. 8 the upper edge area of the retaining plate 4 may be provided with sidewardly outwardly extending holding projections 42 whose outer edge surfaces abut the inner edge surfaces of the projections 28 so as to resiliently engage them in such a way that the projections 28 of the mounting frame 202 also retain the retaining plates 4 and hold them onto the side walls of the bottom part 1 with a predetermined pressure when the cover member 201 is locked onto the bottom part by engagement of the projections 18b. This arrangement prevents unintentional release of the retaining plates 4 during handling or similar operations and always insures germ tightness by firm engagement of the filter mat 3. As shown in FIG. 6 the retaining plates 4 are prevented from movement in longitudinal direction by strip-like projections 10a and 14a extending from the side wall 10 at the opposite ends of the plates 4.

It is noted that the projections 18b as well as 42 and/or the projections 28 are formed so as to be somewhat ramp-like in the area of the cooperating surfaces at the respective lengthwise ends in order to facilitate sliding engagement of the cooperating surfaces.

FIG. 9 again shows, arranged at the front side of the closed and sterilized sterilization box, the safety tag 5 with a pull-off tongue 51 which prevents unlocking of the cover without destroying the safety tag and which therefore, by its damage-free condition, indicates that the cover was not opened since the sterilization procedure up to the opening of the box for the removal of the instruments and that the instruments contained in the box are therefore still sterile.

Figure 9:
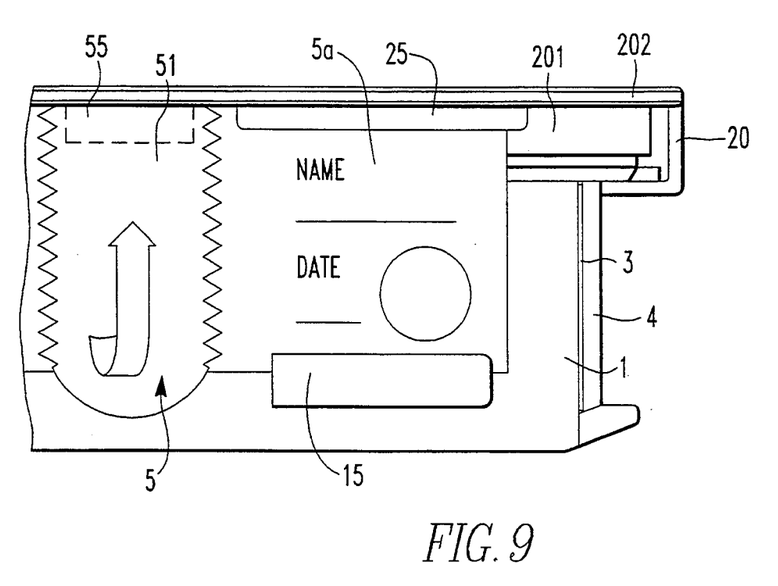
FIG. 9 shows the securing mechanism of the closed sterilization box by means of a locking label.

As shown in FIG. 9 the safety tag 5 is received at its upper and lower edges at its end sections 5a at opposite sides of the pull-off tongue 51 in grooves formed by protruding profiles 15 of the bottom part 1 and profiles 25 of the cover portion 201, which grooves are closed at their outer ends so that the safety tag cannot be moved sidewardly out of these grooves without inflicting damage thereto. Furthermore, the mounting frame 202 of the cover includes a downwardly extending web structure 55 disposed behind the upper section of the pull-off tongue 51 which, with an undamaged safety tag, prevents the mounting frame from being moved forwardly, as indicated in FIG. 1 by arrows, to an unlocking position, since the upper edge areas of the safety tag are retained at both ends by the profile structure 25 of the cover portion 201. The web structure 55 also acts as one of the stops for limiting sliding motion of the mounting frame relative to the cover portion. It cooperates with a recessed surface on the outer edge of the cover member whereas the corresponding stop at the other end of the cover portion is formed, for example, by a small projection 29 which cooperates with the inner circumferential edge 20a of the mounting frame.

As is shown in FIG. 6 the body of the mounting frame 202 flatly disposed on top of the cover portion 201 includes along its longitudinal edges a number of openings 20b which are arranged above the respective projections 28 of the rim structure 20 and the ledges 27 which facilitates manufacture of the mounting frame by injection molding as this eliminates the need for undercutting (the openings 20b are somewhat longer and wider than the respective projections 28 or the ledges). It is pointed out in this connection that the openings 20b are not shown in FIG. 8 since FIG. 8 is a simplified representation, and that the projections 28 and the ledges 27 are shown at the same longitudinal location, which however, in reality, is not the case, as, in reality, the projections 28 and the ledges 27 are displaced relative to one another along the respective longitudinal edge of the mounting frame in order to achieve the manufacturing advantages referred to above.

What is claimed is:

1. A sterilizing container for medical and surgical instruments and apparatus comprising a rigid box of sterilizing temperature-resistant plastic material including a bottom part with side walls and a cover for closing and sealing the bottom part in a germ-tight manner, said bottom part having openings in said side walls which are covered by germ-tight but sterilization vapor or sterilization gas permeable filter layers, said bottom part and said cover being constructed so as to have cooperating engagement structures at one side of said box which retain the cover on said bottom part when said cover is fully closed and at the opposite side of said box resilient cooperating locking structures which are engaged and lock the cover to the bottom part when said cover is closed and upwardly and downwardly open grooves formed respectively on said bottom part below and on said cover above said locking structure and receiving the lower and upper edges of a safety tag upon closing of said cover and side locking members arranged at the opposite edges of said safety tag such that said safety tag is firmly positioned in front of said locking structure when said cover is fully closed, said safety tag being destructible to obtain access to said locking structure for opening said container.

2. A container according to claim 1, wherein said engagement structures consist of at least one knub-like projection extending inwardly from the upper edge of said side wall at said one side of said bottom part and a downwardly extending rib formed on said cover adjacent said side wall engaging the knub-like projection on the side wall of said bottom part.

3. A container according to claim 1, wherein said locking structure comprises a locking strap extending downwardly from said cover and a complementary structure formed on the side of said bottom part for engagement with said locking strap when said cover is closed.

4. A container according to claim 1, wherein said safety tag consists of a rigid material such as cardboard including a pull-off tongue delineated by prestamped perforations.

5. A container according to claim 4, wherein said safety tag has said pull-off tongue formed vertically in the center thereof so as to be disposed above the locking structure and provided with an extension for grasping the pull-off tongue and wherein the retaining means for the safety tag are arranged at opposite sides of said pull-off tongue.

6. A sterilizing container for medical and surgical instruments and apparatus comprising a rigid box of sterilizing temperature-resistant plastic material including a bottom part with side walls and a cover for closing and sealing the bottom part in a germ-tight manner, said bottom part having openings in said side walls which are covered by germ-tight but sterilization vapor or sterilization gas permeable filter layers disposed on the outside of the respective side wall portions of said bottom part and retained in place by retaining plates with openings, the retaining plates being engaged between retaining webs, and ledges projecting from the side wall of said bottom part, said bottom part and said cover being constructed so as to have cooperating engagement structures at one side of said box which retain the cover on said bottom part when said cover is fully closed and at the opposite side of said box resilient cooperating locking structures which are engaged and lock the cover to the bottom part when said cover is closed and retaining means formed on said cover and said bottom part and adapted to receive a safety tag upon closing of said cover such that said safety tag is firmly positioned in front of said locking structure when said cover is fully closed, said safety tag being destructible to obtain access to said locking structure for opening said container.

7. A container according to claim 6, wherein said retaining plate is disposed on said retaining web with one side edge thereof and the other side edge is resiliently engaged by said ledge.

8. A sterilizing container for medical and surgical instruments comprising a rigid box of sterilizing temperature-resistant plastic material including a bottom part with side walls and cover for closing and sealing the bottom part in a germ-tight manner, said bottom part having openings in said side walls which are covered by germ-tight but sterilization vapor or sterilization gas permeable filter layers, said cover being a two-part structure including a cover member having a seal profile structure extending therefrom at its circumference for exgagement with a complementary seal profile structure extending from the side walls of said bottom part, and a mounting frame disposed on said cover member and having opposite side rim portions extending around the side edges of said cover member, said mounting frame being mounted on said cover member so as to be movable relative to said cover member for a predetermined distance and in a direction parallel to said side portions, the side walls of said bottom part having at their top outwardly projecting spaced ledges and said mounting frame side portions having inwardly extending spaced projections fitting through the spaces between said ledges and adapted to engage said outwardly projecting ledges by sliding movement of said mounting frame when said cover member is placed onto said bottom part for locking said cover member with said bottom part.

9. A container according to claim 8, wherein said side rim portions of said mounting frame include grooves which receive the respective edge portions of the cover member and which are formed by ledges projecting inwardly from said side rim portions.

10. A container according to claim 8, wherein said filter layers are disposed on the outside of the respective side wall portions of said bottom part and are retained in place by retaining plates with openings, the retaining plates being releasably mounted on said side walls.

11. A container according to claim 10, wherein one side edge of said retaining plate is disposed on a retaining web of said bottom part and the other side edge of said retaining plate is resiliently engaged by a ledge of said bottom part.

12. A container according to claim 11, wherein said retaining plates are engaged at opposite side edges between retaining webs and ledges projecting from the side walls of said bottom part.

13. A container according to claim 12, wherein said retaining plates are held in longitudinal positions by strip-like projections extending from the side wall of the bottom part at opposite ends of said retaining plates.

14. A container according to claim 12, wherein said retaining plate has at its upper end a number of sidewardly extending holding projections corresponding in arrangement and position to the projections on the respective upper ledge of the side wall of said bottom part, said inwardly extending projections of said side rim portion of said mounting frame engaging said holding projections thereby holding said retaining plate firmly against the side wall of said bottom part.

15. A container according to claim 8, wherein one of the sides of said container which extends transverse to the side walls which have their edges surrounded by said mounting frame side rim portions is provided with a safety tag usable for labeling, said tag including a stamped pull-off tongue in the center thereof providing for side sections at opposite sides of said pull-off tongue, said bottom part side wall having support profile structures for receiving the lower edges of the side sections of said tag and the cover member having support profile structures receiving the upper side sections of said tag and stops projecting from the side wall at opposite ends of said tag to prevent sideward movement thereof, said mounting frame having a web structure projecting downwardly behind said tag so as to prevent movement of said mounting frame relative to said cover member out of its locking position without destruction of said tag.

16. A container according to claim 8, wherein said mounting frame includes a structure flatly disposed on the circumferential edges of said cover member with which said side rim portions are integrally molded, said mounting frame structure having top openings formed therethrough in the area of the inwardly extending projections and the areas of the inwardly projecting ledges which engage the cover member.

17. A container according to claim 8, wherein said mounting frame on top of said cover member has an inner dimension corresponding to the size of the bottom of said bottom part so as to form with the top of said cover member a cavity limited by the mounting frame and complementary to the bottom portion of said bottom part.

* * * * *